US008719056B1

(12) United States Patent
Bartley et al.

(10) Patent No.: US 8,719,056 B1
(45) Date of Patent: May 6, 2014

(54) COMPUTERIZED HEALTH BEHAVIOR REWARD SYSTEM AND METHOD

(75) Inventors: David Bartley, Louisville, KY (US);
Jeremy Watson, Shelbyville, KY (US);
Kirk McIver, Louisville, KY (US)

(73) Assignee: Humana Inc., Louisville, KY (US)

( * ) Notice: Subject to any disclaimer, the term of this patent is extended or adjusted under 35 U.S.C. 154(b) by 449 days.

(21) Appl. No.: 12/752,765

(22) Filed: Apr. 1, 2010

Related U.S. Application Data (60) Provisional application No. 61/165,649, filed on Apr. 1, 2009.

(51) Int. Cl.
*G06Q 50/00* (2012.01)

(52) U.S. Cl.
USPC ................ 705/3; 705/2; 705/14.1; 705/14.37

(58) Field of Classification Search
USPC ....................................... 705/1–37
See application file for complete search history.

(56) References Cited

U.S. PATENT DOCUMENTS

| | | | |
|---|---|---|---|
| 7,953,611 B2 * | 5/2011 | Goodman et al. ................ | 705/3 |
| 2005/0228692 A1 * | 10/2005 | Hodgdon ........................... | 705/2 |
| 2006/0111944 A1 * | 5/2006 | Sirmans et al. ................... | 705/3 |
| 2006/0136258 A1 * | 6/2006 | Horn et al. ........................ | 705/2 |
| 2007/0106538 A1 * | 5/2007 | Holtermann et al. ............. | 705/4 |
| 2008/0189133 A1 * | 8/2008 | Wilson et al. .................... | 705/2 |
| 2008/0201175 A1 * | 8/2008 | Levin et al. ....................... | 705/3 |
| 2008/0255979 A1 * | 10/2008 | Slutzky et al. ................... | 705/35 |
| 2009/0265183 A1 * | 10/2009 | Pollard et al. .................... | 705/2 |

OTHER PUBLICATIONS

Health Incentive Program from Humana Encourages Gradual Changes and Healthier Behaviors, Business Wire, Nov. 13, 2008, 2 pages, Denver, http://www.businesswire.com/portal/site/humana/permalink/?ndmViewId.
Healthy Rewards: New Health Incentive Program Rewards Employees and Employers for Healthy Decision Making, Business Wire, Feb. 27, 2009, 2 pages, Milwaukee, http://www.businesswire.com/portal/site/humana/index.jsp? ndmConfigId.

* cited by examiner

*Primary Examiner* — Mark Holcomb
(74) *Attorney, Agent, or Firm* — Standley Law Group LLP (57) ABSTRACT

A computerized health behavior reward system and method is disclosed. Engagement of rewards program members is based on rewards for participation in a variety of health activities. Health activities are recommended to members based on demographic and health profile information and include general health activities such as participation in fitness programs as well as disease management and clinical programs, educational campaigns, online, interactive, and social networking activities, and community based activities. Each activity may relate to a particular participation event so that members are rewarded for enrolling in a program as well as for ongoing participation. Members earn points for each health activity in which they participate. The points are accumulated in a rewards account accessible from a web site portal and can be redeemed. The computerized system and method provides flexibility to allow a reward program sponsor to respond to different needs of the rewards program population at the consumer level.

10 Claims, 8 Drawing Sheets

| Activity and Earnings Summary | Events Completed | | Earnings | |
|---|---|---|---|---|
| | Month | Plan Year to Date | Month | Plan Year to Date |
| Rewards Opt-in | 24 | 210 | 24,000 | 210,000 |
| Humana Health Assessment Completed | 20 | 188 | 50,000 | 470,000 |
| Electronic Preferences Selected | 12 | 164 | 12,000 | 164,000 |
| Health Coaching Completion | 10 | 134 | 50,000 | 670,000 |
| Disease Management Participation | 1 | 13 | 2,500 | 32,500 |
| Personal Nurse Participation | 0 | 12 | 0 | 60,000 |
| Preventive/Maintenance Care Completion | 2 | 10 | 8,000 | 40,000 |
| Survey Completion | 3 | 9 | 3,000 | 9,000 |
| <hold for additional opportunity> | 1 | 5 | 1,500 | 7,500 |
| Total Earnings Activities | 73 | 745 | 151,000 | 1,663,000 |
| Average per Participant | | 3.6 | | 7,957 |

COMPUTERIZED HEALTH BEHAVIOR REWARD SYSTEM AND METHOD

CROSS-REFERENCES TO RELATED APPLICATIONS

This application is a non-provisional patent application claiming the priority benefit of U.S. Provisional Patent Application Ser. No. 61/165,649, filed Apr. 1, 2009, titled SYSTEM AND METHOD FOR USING REWARDS TO ENCOURAGE HEALTHY BEHAVIOR, which is incorporated herein by reference in its entirety.

FIELD OF THE INVENTION

The present invention relates generally to computerized reward program systems and methods. In particular, the disclosed embodiment is a computerized health behavior reward system and method for offering and tracking rewards for a member population to encourage healthy behaviors.

BACKGROUND OF THE INVENTION

Preventable illnesses and accidents constitute a large percentage of US healthcare costs. Although many illnesses and accidents are preventable, most available healthcare dollars are spent on illnesses and restoration while only a very small percentage of healthcare dollars are devoted to prevention. One way to substantially reduce healthcare costs in the US is to prevent illnesses and accidents from occurring. Because preventive efforts can have a substantial impact on healthcare costs, many companies that cover the healthcare costs of individuals and groups of individuals have introduced "wellness incentives" to their covered members, employees, etc.

Preventive efforts that many companies have adopted include having individuals complete health risk assessments and participate in health management programs for various illnesses and diseases. Wellness incentives are tied to the preventive efforts, and individuals are rewarded when they complete or participate in a specified activity. Point values may be assigned to various activities and awarded to individuals when they complete or participate in the activities. Points may then be redeemed for items such as sporting goods, electronics, house wares, etc. or discounts or gift certificates to national or specialty retailers. The array of reward options available to individuals may be significant to increase the likelihood that each individual finds an item that he or she likes and for which he or she is willing to work.

Although many companies have adopted wellness incentive or reward programs to reward individuals for participation in various healthy activities, typically the various health activities are not appropriate for all individuals. Each covered member may have specific health needs based on sex, age, and known health conditions (e.g., diagnosed illnesses or diseases, chronic conditions, etc.) Certain disease management programs may be appropriate for some members while informational or exercise programs may be appropriate for other members. It is important for individuals to be directed to the program or programs that meet their needs. Members are more likely to participate in programs that meet their needs and that are beneficial to them and therefore, increase the likelihood that they will receive a reward.

Health reward systems and methods today typically rely on individuals to select and enroll in programs of their own choosing. Individuals may be provided with information about various health programs and encouraged to participate in specific programs based on their known health conditions. For a variety of reasons, however, they may choose not to participate. Some individuals may not see a need to participate in the programs. Other individuals may not understand the health benefits of the programs. For some individuals, the availability of a health benefit may simply not be enough to encourage them to participate, even if the program is appropriate. Finally, when presented with so many different programs and options, they may not understand which programs actually meet their needs and therefore, simply choose not to participate at all.

There is a need for a computerized health behavior reward system and method that allows individuals to learn about and earn rewards for participating in various health programs. There is a need for a computerized health behavior reward system and method that matches individuals to appropriate health programs, offers them opportunities to enroll and participate, and rewards them for enrolling and participating. There is a need for a computerized health behavior reward system and method that uses various criteria to segment a member population into various groups according to their needs and to offer activity rewards based on groups. There is a need for a computerized health behavior reward system and method that records data related to enrollment and participation activities for various health programs and that evaluates the program participation data to determine whether additional programs may be appropriate for an individual. There is a need for a computerized health behavior reward system and method that encourages individuals to become engaged in their own health by rewarding them for participation in a variety of health programs.

SUMMARY OF THE INVENTION

A computerized health behavior reward system and method is disclosed. In an example embodiment, a reward program supported by the computerized system and method uses a phased approach to familiarize participants with health activities and then rewards them for participating in the activities. Each reward provides encouragement to an individual as the individual takes action toward improving his or her health. The reward program may be sponsored by a party that determines what health activities may be offered as well as the rewards associated with the activities. The sponsor may be an insurance company that provides insurance services to individual customers or a customer of an insurance company that provides insurance to a group of individuals (e.g., an employer).

In an example embodiment, engagement of individuals is based on rewards for participation in general health programs as well as specialized health programs. Two or more program categories are defined and within each category, specific activities are defined. A single health program may be subdivided into activities or events with related participation points for each activity (e.g., enrollment, renewal, 1-month participation, completion of a goal, etc.) Reward points are associated with each activity within a program.

Members of an insured or other population may be eligible for general health as well as specialized health activities. Specialized health activities are suggested to individuals based on demographic or profile information or based on an analysis of their specific health conditions. Members are rewarded for participating in the activities. Members that have not started participating in a program that is appropriate for them may be rewarded for completing an enrollment activity related to the program. Members may also be rewarded for completing a goal activity related to a program. In addition, ongoing participation may be rewarded. The incorporation of specialized health activities into the reward program results in engagement of individuals based on their specific needs. Individuals earn points for each health activity in which they participate and are then provided with opportunities to redeem the points.

The computerized system and method allows individuals to have a more personalized experience the more engaged they become in the reward program. Members may be rewarded initially for completing a health assessment and then receive further health activity recommendations based on their answers and assessment data. Rewards are offered to encourage the member to enroll in the programs, to continue participation in the programs, and to reach goals related to the programs. The computerized system and method may further suggest types of rewards based on the individual's lifestyle, current exercise routines, health conditions, age, gender, and location. Rewards may also be provided for a variety of events such as birthdays, anniversaries, holidays, and even for working out.

The computerized health behavior reward system and method provides flexibility to allow a reward program sponsor to respond to different needs of an insured population at the consumer level. The reward program may include general health activities as well as specialized health activities so all members of the insured population may be engaged in their health. A variety of activities result in rewards for the individual so that the more a member participates in the activities, the greater the reward.

DETAILED DESCRIPTION OF EXAMPLE EMBODIMENT(S)

Figure 1:
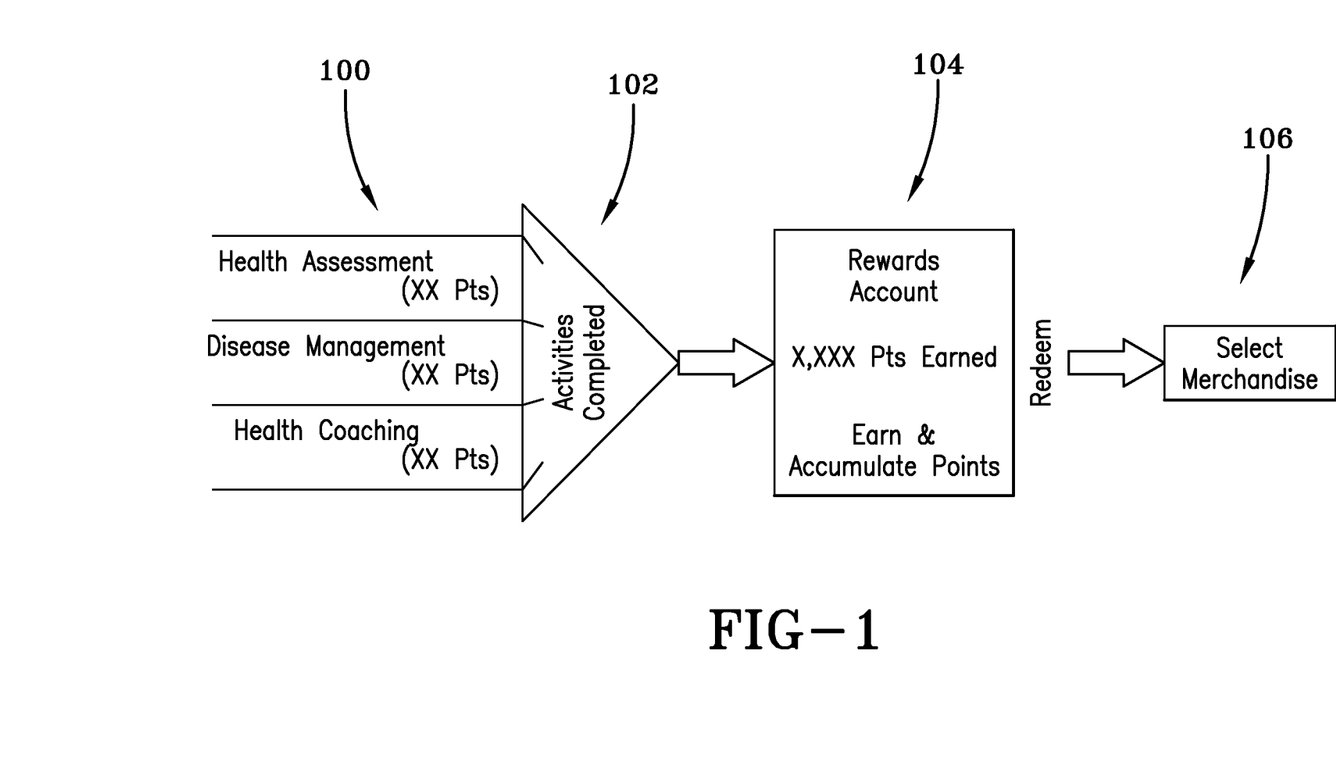
FIG. 1 is a block diagram of the primary components of a reward program according to an example embodiment.

Referring to FIG. 1, a block diagram of the primary components of a computerized reward program according to an example embodiment is shown. Members of a reward program accumulate points for participating in various health related activities 100 such as completing a health risk assessment, enrolling and participating in a disease management program, or participating in a health coaching program (telephonic or online). Information regarding the activities they complete 102 is stored in a rewards account 104. The points that each member earns for each activity may be redeemed for rewards such as merchandise or discounts 106.

Figure 2:
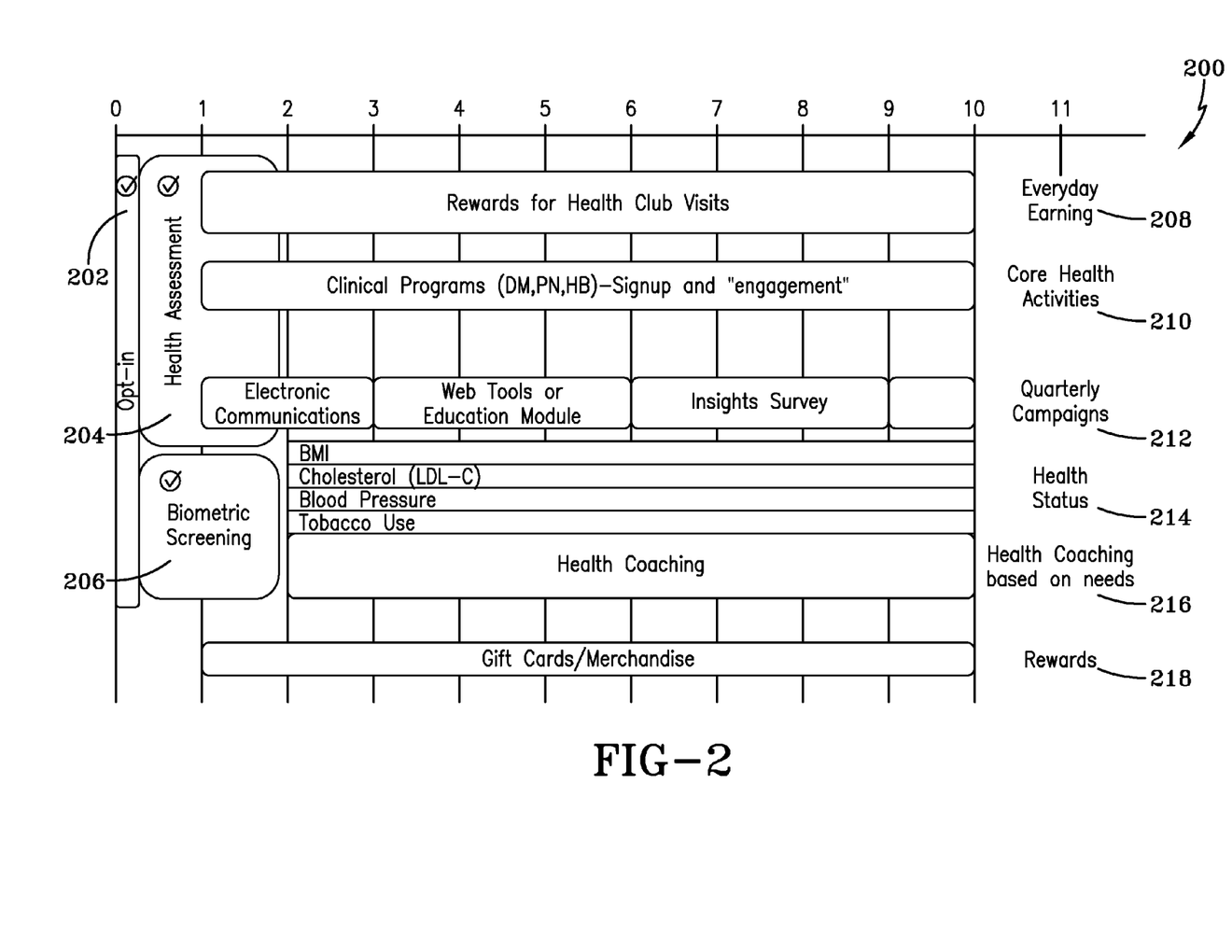
FIG. 2 is a block diagram of a reward program design according to an example embodiment.

Referring to FIG. 2, a block diagram of a reward program design according to an example embodiment is shown. In an example embodiment, various health activities are promoted throughout the calendar year 200. Initially, members of an insured or other population opt-in to the reward program 202.

Part of the opt-in procedure may involve the members agreeing to receive communications about the program electronically. Completing the opt-in procedure may result in a first reward for the member and agreeing to receive communications electronically may result in a second reward. Members may be asked to complete a health assessment 204 which is also eligible for a reward. In the health assessment, a member provides identifying and demographic information and answers questions about various health factors. For example, the member may be asked to provide height and weight information as well as information about alcohol and tobacco use, known heart, blood, or other conditions, prior illnesses or accidents, etc. The health assessment data is stored in a database and may be used to identify health activities relevant to the member's health factors and conditions.

Another activity in which a member may be invited to participate is a biometric screening 206. The biometric screening may include requesting health status information 214 such as a member's height and weight, a blood pressure reading, cholesterol and glucose levels, etc. Other health activities include health counseling and coaching through online and/or telephonic systems 216. Participation in the screening and coaching activities may be rewarded.

Certain activities may be categorized as "general engagement activities," "general health activities," or "everyday earning" 208 activities. Such activities may be used to engage the entire member population. These activities are typically more preventive in nature and may or may not have an immediate and direct impact on health. The goal with these activities is to get members engaged in their own health and health education. As such, the immediate impact on health insurance claims may be lower, but they provide a greater long-term opportunity for the sponsor of the reward program to get its members involved in their health and the reward program.

A specific number of reward points may be assigned to each activity in the general health category and may include activities such as health club visits. A member may be rewarded for every health club visit he or she makes during a calendar year. To receive rewards, members may register with a health club in the sponsor's network and indicate that they are part of the reward program. Members may then be rewarded monthly based on the number of visits they make in a month. For example, a member that visits the club eight times a month may be awarded 500 bonus points. Twelve visits in a month may result in an award of 1,000 bonus points.

Other activities may be categorized as "specialized engagement activities," "specialized health activities," or "core health activities" 210. Certain members within the member population may have specific needs related to their health conditions. Some members may require an activity as simple as an annual checkup while other members have a need for an activity that is part of a program for managing a specific disease. Rather than broadcasting these activities to the entire member population, the computerized system and method targets members that may have a need for such health activities. Furthermore, members are offered rewards at the time they are engaged in making the decision regarding the activity to increase the likelihood that they will enroll in the program and continue to participate. By introducing a reward opportunity at the time of decision making, the reward program more effectively influences changes in the behavior of the member population.

In another aspect of the claimed invention, the reward program comprises campaigns throughout the calendar year 212. In an example embodiment, campaigns are introduced quarterly. A first campaign may involve electronic communications regarding various general health activities while another campaign involves introducing web tools or education modules at a web site. Another example campaign may involve completing an insights survey to obtain feedback from members. The feedback may be used to improve existing activities and programs, to determine whether there is a need for additional activities or programs, to revise the rewards offered for various activities or programs, or to determine whether a particular member has additional needs that could be met through one or more activities or programs. Participation in each campaign allows an individual to accumulate additional rewards. Participation may include reviewing information, completing questionnaires, etc.

Whether new campaigns or identification of specific health needs, each member is presented with a list of activities that he or she can complete to receive rewards. This list is dynamic according to the member's needs and is generated by the computerized system and method using data from various information sources. For example, females over age 40 are presented with a reward opportunity for a mammogram. Females that are pregnant may be presented with a reward opportunity for enrolling and participating in a pre-natal program. All members over age 50 may be presented with a reward opportunity for completing a colon cancer screening. Referring to Table 1, a list of sample activity categories and sample activities within each category is provided. Each activity may have an associated reward point value. A program may have multiple activities associated with it such that a member is rewarded for enrolling in the program and then completing additional participation events for the program (e.g., visiting a doctor, attending meetings).

TABLE 1

Categories and Activities

| Category | Activity | Points |
|---|---|---|
| Clinical | Asthma Disease Management Enrollment | 1,000 |
| Clinical | Congestive Heart Failure Disease Management Enrollment | 1,000 |
| Clinical | Diabetes Disease Management Enrollment | 1,000 |
| Clinical | Coronary Artery Disease Management Enrollment | 1,000 |
| Clinical | Chronic Kidney Disease Management Enrollment | 1,000 |
| Clinical | Asthma Disease Management Engagement | 1,500 |
| Clinical | Congestive Heart Failure Disease Management Engagement | 1,500 |
| Clinical | Diabetes Disease Management Engagement | 1,500 |
| Clinical | Coronary Artery Disease Management Engagement | 1,500 |
| Clinical | Chronic Kidney Disease Management Engagement | 1,500 |
| Clinical | Healthcare for Expectant Mothers Enrollment | 1,000 |
| Clinical | Personal Nurse Enrollment | 1,000 |
| Clinical | Personal Nurse Engagement | 1,500 |
| Fitness | 8 Health Club Visits | 500 |
| Fitness | 12 Health Club Visits | 1,000 |
| Fitness | Self-Reported Health Activities | 200 |
| Fitness | Walking Trails | 400 |
| Fitness | Device with Uploaded Data | 500 |
| Fitness | Challenges - group | 1,000 |
| Fitness | Challenges - individual | 1,000 |
| Fitness | Run, Walk, Wheelchair a Race | 1,000 |
| Fitness | Bicycle Usage | 1,000 |
| Health | Biometric Screening | 1,000 |
| Health | Biometric Results - Cholesterol Ideal | 1,000 |
| Health | Biometric Results - BMI Ideal | 1,000 |
| Health | Biometric Results - Blood Pressure Ideal | 1,000 |
| Health | Biometric Results - Tobacco Free | 1,000 |
| Health | Mammogram | 1,500 |
| Health | Pap Smear | 1,500 |
| Health | Colonoscopy | 1,500 |
| Health | Smoking Cessation Program Online | 1,500 |
| Health | Weight Management Program Online | 1,500 |
| Health | Back Care Program Online | 1,500 |
| Health | Stress Management Program Online | 1,000 |

TABLE 1-continued

Categories and Activities

| Category | Activity | Points |
|---|---|---|
| Health | Nutrition Program Online | 1,000 |
| Health | Smoking Cessation Program by Telephone | 1,500 |
| Health | Weight Management Program by Telephone | 1,500 |
| Health | Back Care Program by Telephone | 1,500 |
| Health | Stress Management Program by Telephone | 1,000 |
| Health | Nutrition Program by Telephone | 1,000 |
| Health | BMI Calculator | 500 |
| Health | Stay Smart Stay Healthy Videos (reward for each) | 500 |
| Health | Walk-in Clinic Visits | 500 |
| Health | Sleep Program | 1,000 |
| Health | New Baby and Pre-natal | 1,000 |
| Health | Child Immunizations | 1,000 |
| Health | Learning first aid, CPR etc. | 500 |
| Health | Meal Plans - Set, Track & Complete | 500 |
| Lifestyle | Fitness Tips (tip of the day) | 500 |
| Lifestyle | Nutrition Tips (tip of the day) | 500 |
| Lifestyle | Healthy Recipes | 500 |
| Lifestyle | Farmers Markets - Find | 500 |
| Lifestyle | Calorie Counter and Other Calculators | 500 |
| Lifestyle | Food Calorie Content - Restaurants etc. | 500 |
| Lifestyle | Other Lifestyle items | 500 |
| Lifestyle | Brain Games | 500 |
| Lifestyle | Activity Games | 500 |
| Lifestyle | Reward Taking Bus, Car-pooling, Biking, Walking | 500 |
| Lifestyle | Behavioral Change Offerings | 500 |
| Lifestyle | Employee Incentives | 500 |
| Overall | Suggestions/Website Feedback | 500 |
| Overall | Monthly Newsletter | 500 |
| Overall | Surveys | 500 |
| Overall | Contributions to Health Savings Account | 500 |
| Overall | Access Card Activation (health savings account, personal care account, and healthcare flexible spending account | 500 |
| Overall | Participation in Activities at Guidance Centers | 500 |
| Social Media | Social Networking on Health Topics | 500 |
| Social Media | Health Blog/Message Board Participation | 500 |
| Partnerships | Four Square Deal - reward for activity | 500 |
| Partnerships | Health Device Use (pedometer, GPS fitness tracking) | 1,000 |
| Partnerships | Health Mobile Applications | 500 |
| Partnerships | Partner Health Services | 500 |
| Partnerships | Health Tracking and Comparison Services | 500 |
| Partnerships | Health Books and Materials | 500 |
| Partnerships | Health Website Visits | 500 |
| Partnerships | Recycling/Environmental Activities | 500 |
| Partnerships | Point of sale Discounts from Healthy Merchants | 500 |
| Partnerships | Charitable Activities | 500 |
| Partnerships | Career Well-being Activities | 500 |
| Profile Information | Reward Program Enrollment | 1,000 |
| Profile Information | Reward program Enrollment Bonus within 120 days | 1,500 |
| Profile Information | Health Assessment | 2,000 |
| Profile Information | Health Assessment Bonus within 120 days | 2,500 |
| Profile Information | Health Alerts | 500 |
| Profile Information | Birthday Bonus | 500 |
| Profile Information | Renewal Bonus | 500 |
| Profile Information | Multiple Insurance Products (dental, vision, etc) | 500 |
| Transparency Tools | Electronic Explanation of Benefits Option | 500 |
| Transparency Tools | Electronic Statement Option | 500 |
| Transparency Tools | Electronic Notification of Other Insurance Option | 500 |
| Transparency Tools | Electronic Maximize Your Pharmacy Benefits Option | 500 |
| Transparency Tools | Drug Pricing Details Tool | 500 |
| Transparency Tools | Pharmacy Locator Tool | 500 |
| Transparency Tools | Health Record Accessed | 500 |
| Transparency Tools | Prescription Calculator | 500 |
| Transparency Tools | Find a Doctor Service | 500 |
| Transparency Tools | Compare Hospitals Tool | 500 |
| Transparency Tools | Compare Doctors Tool | 500 |
| Transparency Tools | Insights Survey | 500 |
| Transparency Tools | Generic Prescriptions | 1,000 |

As indicated in the activity list, points may be awarded for different participation activities or events within a program. For example, points may be awarded for enrolling in a program and then for ongoing participation in a program. Points may also be awarded for renewing enrollment in a program. Additional incentives may be awarded for enrolling within a specified time period (e.g., 120 days). The offering of rewards in connection with a variety of activities for one or more program allows individuals to be rewarded frequently. The use of frequent rewards allows individuals to become engaged in their own health very quickly and to continue that engagement.

The types of health-related activities that may be rewarded are numerous so that all members of the reward program are provided with an opportunity to receive rewards for their participation. The variety of opportunities allows each member to be engaged in a way that is individually meaningful and relevant. Many of the activities involve wellness and preventive care activities so that members are engaged in their health and the reward program even when they are not sick. As members become familiar with and active in the reward program while they are well, they are more likely to remain involved if they become ill. They further continue the engagement in their own health.

Figure 3:
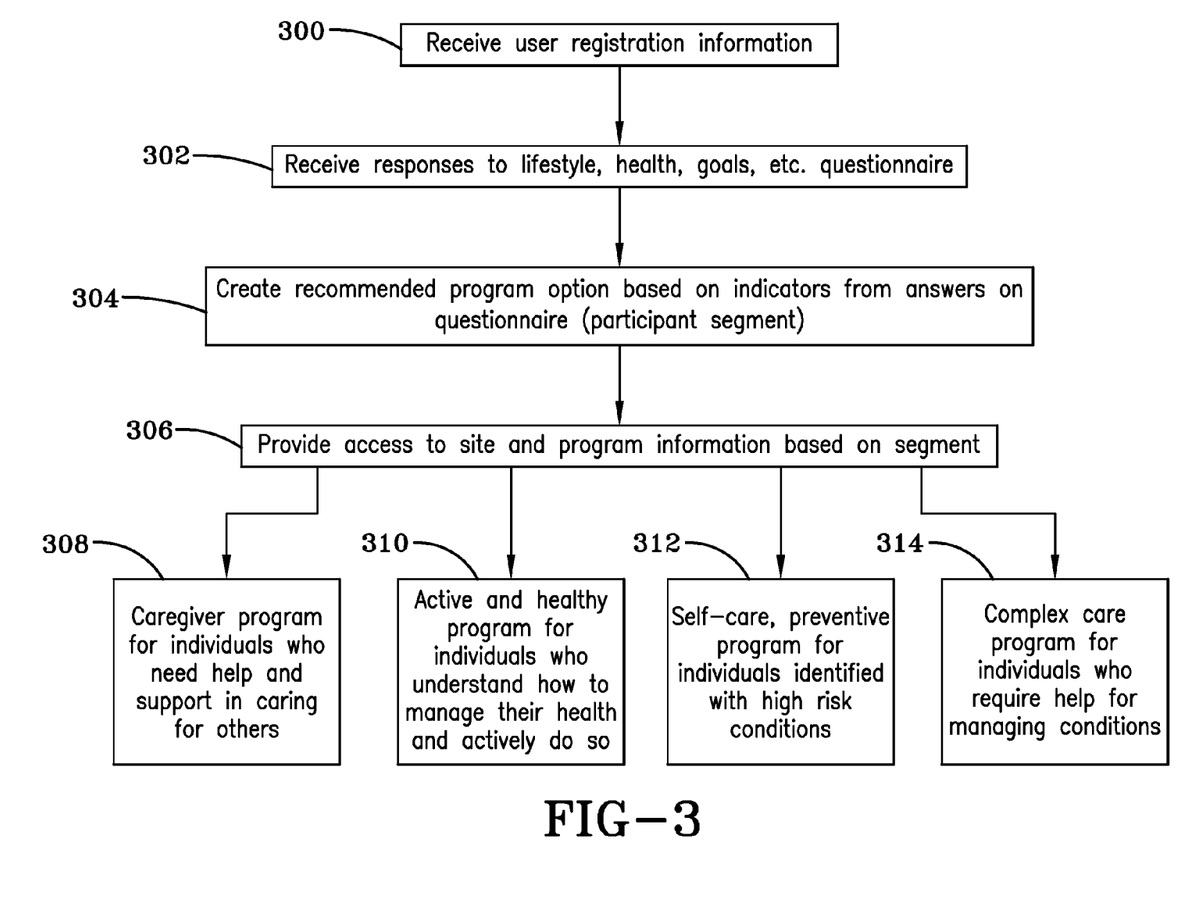
FIG. 3 is a flowchart of a segmentation process for reward opportunities according to an example embodiment.

Referring to FIG. 3, a flowchart of a segmentation process for reward opportunities according to an example embodiment is shown. The segmentation process results in the identification of members for activities that are targeted to their specific needs. Member registration information 300 as well as member questionnaire data 302 is received at a computer server where the segmentation process executes. Reward accounts for each member may be established at a database. The member registration and member questionnaire data may be stored in a separate reward account for each member.

Data from various computerized systems and databases is aggregated at a rewards server to identify activities that are relevant for various segments of the member population 304. For example, each clinical program included in the reward program may have eligibility criteria for participation in the program. The eligibility criteria may relate to specific demographic data and health conditions (e.g., over 45, elevated blood pressure, etc.) as well as whether the program is covered under an insurance plan. Various computerized processes executing at other servers may be employed to collect the eligibility criteria and identify the members from the population eligible for the various programs. The rewards server uses this information from various other servers to apply to rewards participants. The rewards server executes a process to "flag" or identify participants as eligible for certain activities and then track the participants' progress in engaging in and completing those activities. Individuals that do not have a need to participate in disease management or clinical programs may still be provided with opportunities to participate in general health activities such as health club visits or other fitness activities.

The segmentation process receives identifying data for individuals that have been identified as eligible for the programs but have not yet enrolled or engaged in the programs. Information about members that are eligible but not yet enrolled or engaged provides a reward opportunity. In addition, member responses to the questionnaire may be considered in the activity recommendations 304. Certain answers or information from the questionnaire may serve as indicators for the types of activities that are most likely to be of interest to the member and therefore, determine the applicable segment.

Each group of segmented members may be informed about a specific activity and further, offered a reward for enrolling or engaging the program at the time the activity is presented 306. Members that may not be motivated solely by the health benefits of the activity may be motivated by the associated reward and decide to enroll or engage in the program at the time the offer is presented. Table 2 provides a list of example segments and programs.

TABLE 2

Example Member Segments and Programs

| Member Segment | Program |
| --- | --- |
| Members that need help and support in caring for others | Caregivers Program 308 |
| Members that understand how to manage their health and actively do so | Active Management Program 310 |
| Members identified with high risk conditions | Self-care, Preventive 312 |
| Members that require help managing a specific health condition | Clinical Program 314 |

The process for enrolling or engaging in programs varies depending upon the program. Some programs may have online enrollment or registration procedures. Members may access a reward account portal and make their selections of enrollment or engagement activities through the portal. For example, members that would like to participate in health club programs may register with a health club in the sponsor's network and indicate that they are part of the reward program. For other activities, members may be contacted by a representative that is informed of the member's eligibility. For example, members in need of care management for a specific condition may be contacted by a nurse who informs the member of the available service. If the member agrees to participate at the time he or she is contacted, the nurse may complete the computerized enrollment process for the member. The member's reward account may then be updated so that the member receives the enrollment activity reward. The service may be a disease management program or a personal nurse program.

Figure 4:
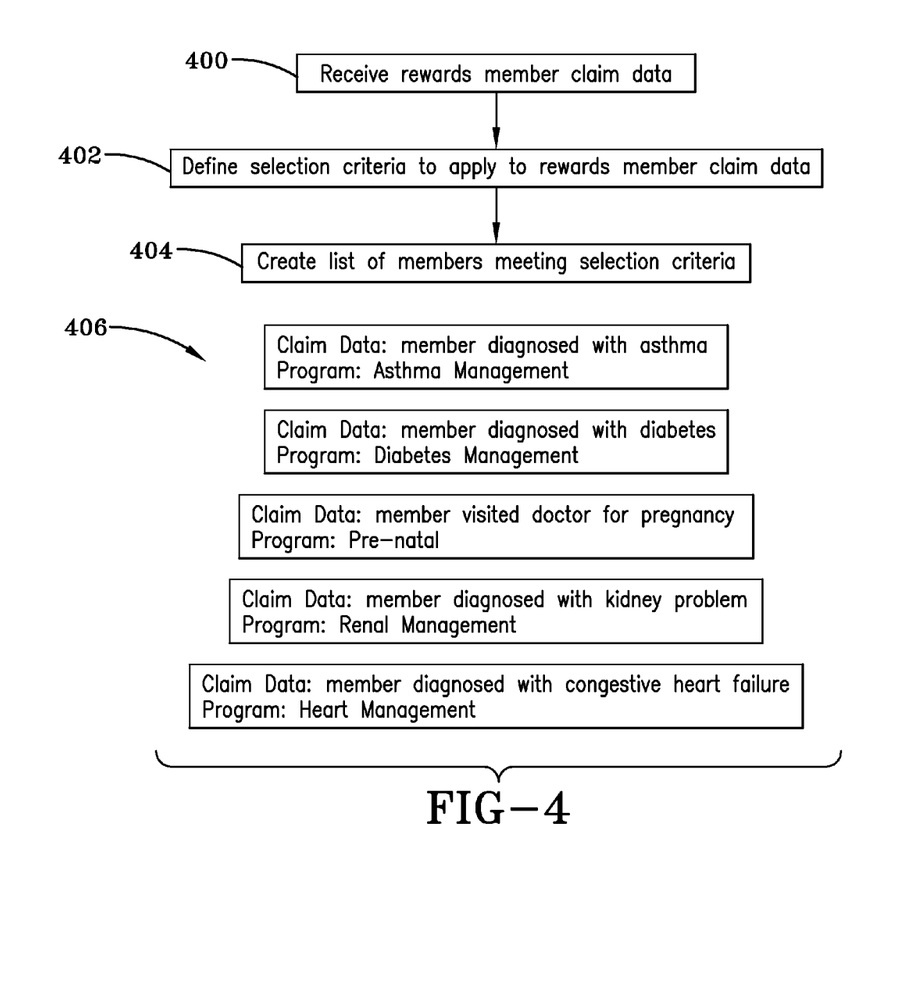
FIG. 4 is a flowchart of a selection process according to an example embodiment

Referring to FIG. 4, a flowchart of a selection process according to an example embodiment is shown. The selection process may be used to match members with various programs. Health claims data 400 as well as other personal data (e.g., questionnaires) is analyzed to determine which programs are appropriate for a member. Selection criteria for the programs are applied to the member claim data for the various programs 402. In an example embodiment, the output for the selection process is a list of members that meet the selection criteria for a program 404.

Various items within the claim data such as a specific diagnosis (e.g., asthma, diabetes, kidney problem, or congestive heart failure) or event (e.g., pre-natal checkup) is matched with program selection criteria to identify an appropriate program 406. Activities associated with the programs may then be presented to the members based on their program matches. For example, members that have not yet enrolled in a program may be presented with an enrollment activity. If the member agrees to the enrollment activity, the member's reward account is updated to reflect the member's selection of the enrollment activity and award of the points associated with the activity. Member responses to activities may be tracked to determine a member's level of participation in a particular program.

Figure 5:
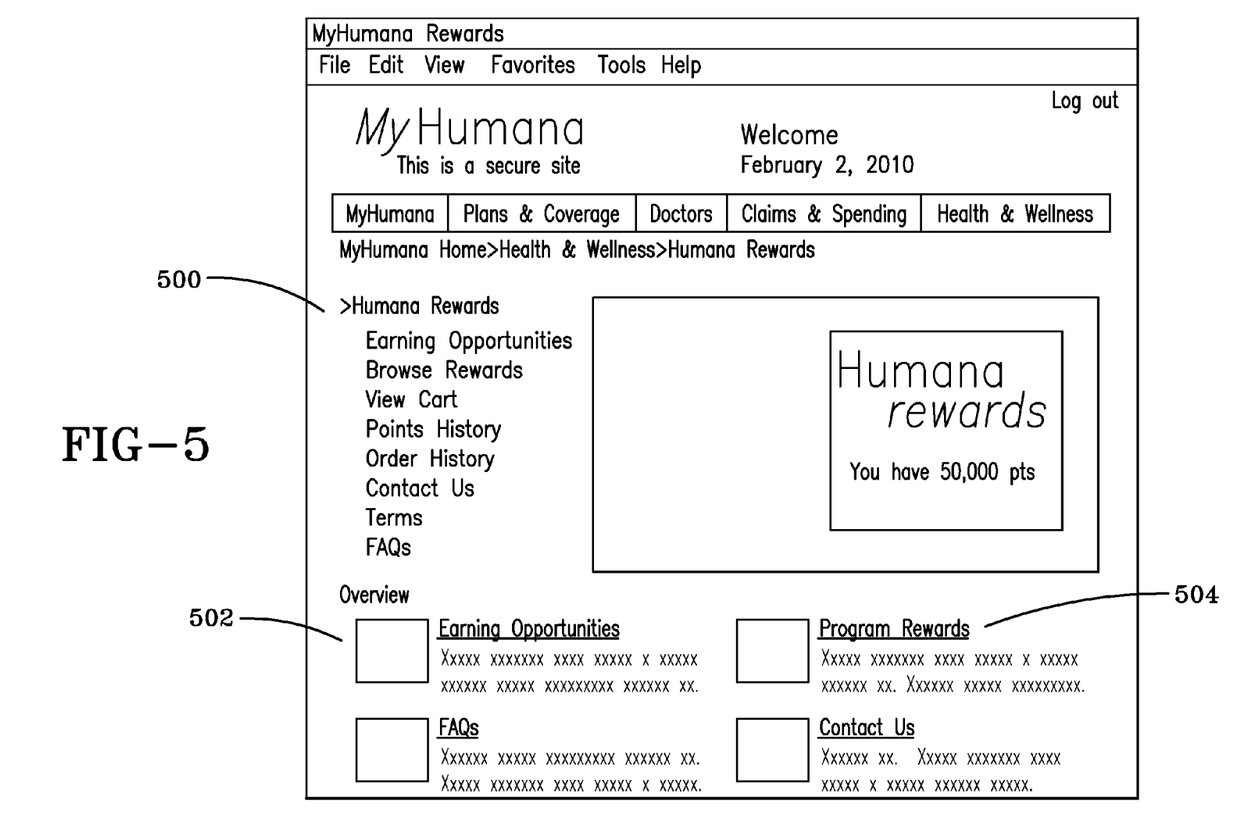
FIG. 5 is a screen shot of a reward account portal for an example embodiment.

Referring to FIG. 5, a screen shot of a reward account portal for an example embodiment is shown. Members that enroll in the reward program may view details regarding their reward account 500 by accessing it through a web site. Each activity in which the member participates may be listed as well as the participation date and associated reward. Members may view information about the reward opportunities 502 that have been selected for them as well as redeeming their reward points 504. Various aspects of the reward program may be supported by the computerized system and method including member account management. Reward account data may be reviewed and analyzed periodically by the reward program administrator to determine participation levels, identify new activities and rewards, identify possible enhancements to the program, etc.

Figure 6:
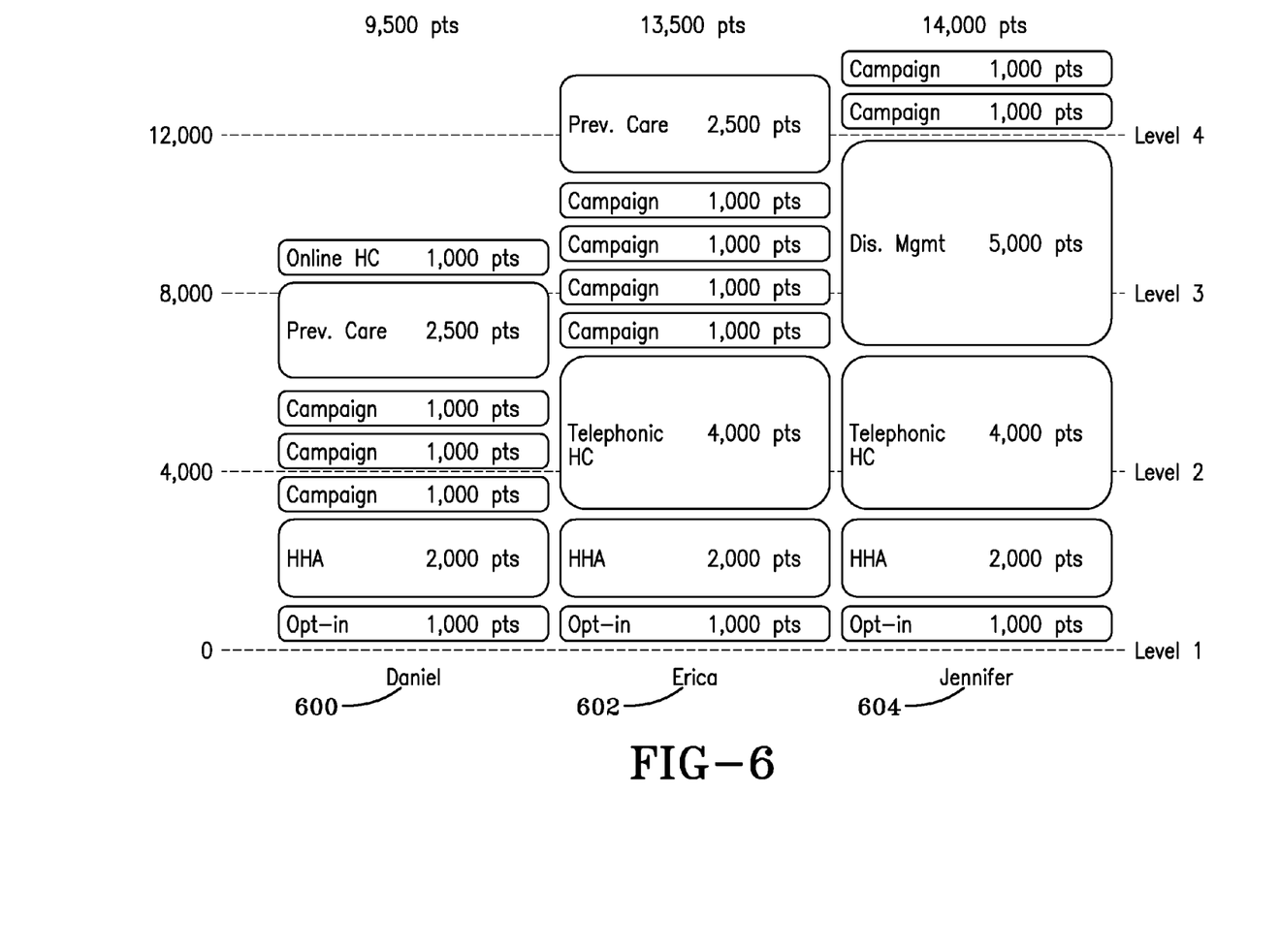
FIG. 6 is a diagram illustrating reward program account data according to an example embodiment.

Referring to FIG. 6, a diagram illustrating reward program account data according to an example embodiment is shown. Each member of the member population is presented with different reward opportunities and for a variety of reasons, selects different opportunities. As a result, the reward program is different for every member. For example, a first member 600 may accumulate points for participation in preventive care activities and in campaigns. A second member 602 may accumulate points for participation in preventive care activities and campaigns as well as telephonic health coaching activities. A third member 604 may accumulate points for participation in telephonic health coaching activities as well as disease management activities. All three members may receive points for opting in to the reward program (1,000 points) and completing a health assessment (2,000 points). The activities are targeted toward members according to their needs and results in a different user experience for each member.

Figure 7:
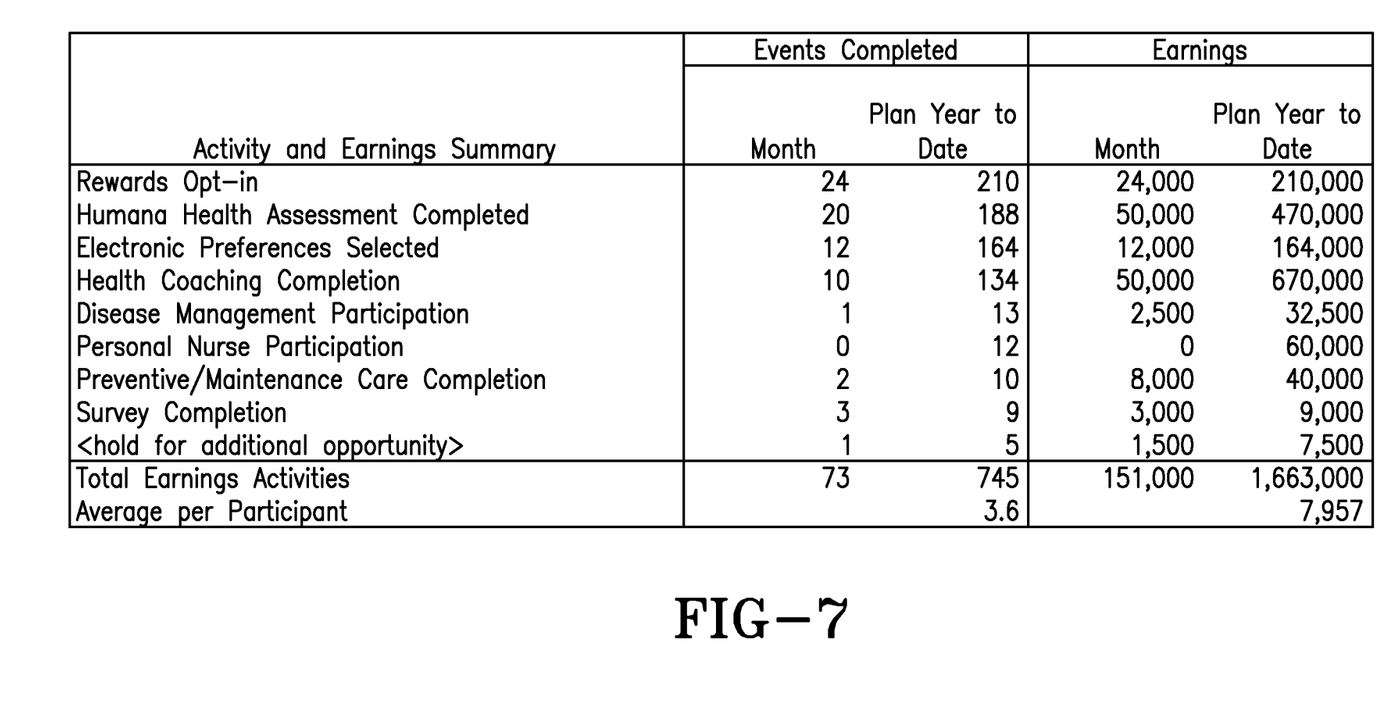
FIG. 7 is a sample rewards program sponsor summary statement according to an example embodiment.

Referring to FIG. 7, a sample rewards program sponsor summary statement according to an example embodiment is shown. The summary statement identifies various activities related to the rewards program and related participation data. The summary statement provides feedback to the sponsor and may assist the sponsor in modifying and improving the rewards program.

Figure 8:
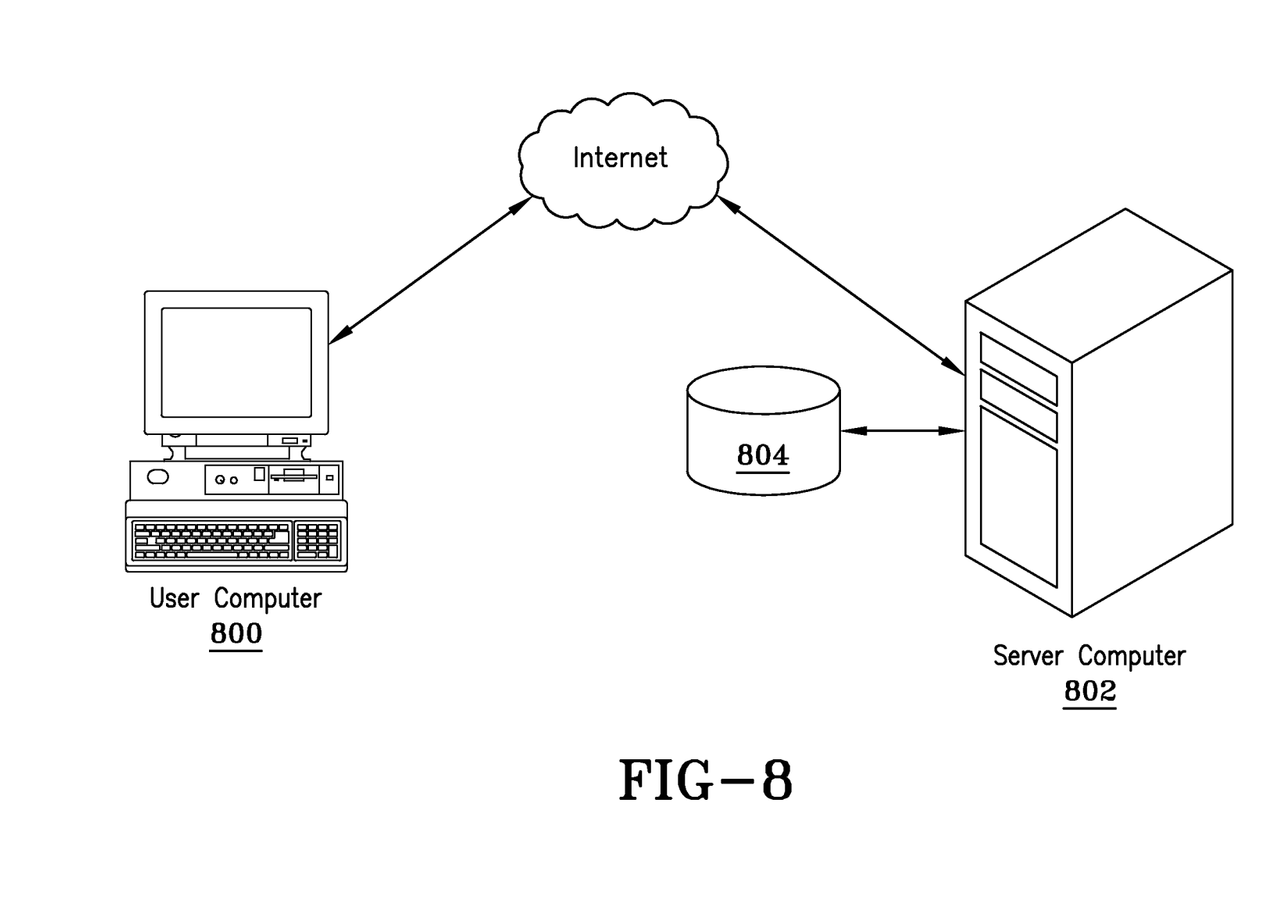
FIG. 8 is a block diagram of computer components according to an example embodiment.

Referring to FIG. 8, a block diagram of computer components according to an example embodiment is shown. Members of the reward program may access the reward program server 802 using their personal computers 800 or other computing devices. Depending upon the size of the rewards program, multiple servers may be used to service the member base. Member rewards account data as well as data related to reward program may be stored at one or more databases 804 accessible to the server 802 or servers.

The computerized system and method of the present invention allows an insurance company or sponsor to engage members in their health by rewarding a variety of healthy activities. Because wellness and preventive care activities as well as activities for clinical and disease management programs are incorporated into the reward program, all members are provided with opportunities to become engaged. When the member is contacted about the program, he or she is also informed of the participation incentive. The incentives for activities are offered at the time decisions are made to encourage behavior change.

Having shown and described a preferred embodiment of the present invention, those skilled in the art will realize that many variations and modifications may be made to the described invention and still be within the scope of the claimed invention. Thus many of the elements indicated above may be altered or replaced by different elements which will provide the same or substantially the same result and fall within the spirit of the claimed invention. The types and nature of the activities that are offered may be changed and fall within the spirit of the claimed invention. The programs and activities that are offered as well as the segmentation process may be varied to meet the needs of the sponsor and its member population and fall within the spirit of the claimed invention. Therefore, as can be understood from a review of the foregoing description and accompanying drawing figures, the computerized system and method supports a reward program to encourage healthy behavior. Consequently, while certain exemplary embodiments of the present invention are described in detail above, the scope of the invention is not to be considered limited by such disclosure, and modifications are possible without departing from the spirit of the invention as evidenced by the following claims:

What is claimed is:

1. A computerized method for rewarding health behaviors comprising:
   (a) defining in a computer a plurality of health programs comprising for each health program identifying:
      (1) identification data for said health program;
      (2) participation criteria for said health program; and
      (3) a plurality of health activities for each of said programs selected from the group consisting of:
         (i) an enrollment activity; or
         (ii) a participation activity following an enrollment activity;
      wherein said health programs are selected from the group consisting of:
         (i) a preventive health program;
         (ii) a disease management program;
         (iii) an informational program regarding a health condition;
         (iv) a health assessment program;
         (v) a health coaching program;
         (vi) a health screening program;
         (vii) an exercise program;
         (viii) a wellness program: and
         (ix) a web-based health tool program;
   (b) associating at said computer a reward with each of said health activities;
   (c) creating at said computer reward accounts for members of a rewards program;
   (d) executing at said computer a segmentation process to identify a segment comprising a plurality of members from a member population to target for participation in at least one of said health programs, said members identified for said segment based on an analysis of:
      (1) member health claim data; and
      (2) participation criteria for said least one of said health programs;
   (e) generating at said computer a list of members in said segment;
   (f) generating at said computer an offer to participate in said at least one of said health programs;
   (g) after said list and offer to participate are generated, transmitting to each member on said list said offer to participate;
   (h) receiving at said computer responses from members in said segment to said offer to participate in said least one of said health programs; and
   (i) updating at said computer said reward accounts for at least one of the following:
      (1) members in said segment completing an enrollment activity; and
      (2) members in said segment completing a participation activity that is part of a health activity after completing an enrollment activity;

(j) wherein updating said reward accounts comprises issuing points that vary for each completed activity and are redeemable for merchandise, discounts or gift certificates.

2. The computerized method of claim 1 wherein said plurality of health programs are further selected from the group consisting of:
   (1) general health programs appropriate for all members; and
   (2) specialized health programs for members with specified health conditions.

3. The computerized method of claim 1 wherein receiving at said computer responses from said members of said segment comprises receiving responses through a reward account portal for said members.

4. The computerized method of claim 1 wherein receiving at said computer responses from said members of said segment comprises receiving at least one response through a computerized enrollment process completed for the member by a third party.

5. The computerized method of claim 1 wherein an offer to participate in said at least one of said health programs comprises an offer to complete an enrollment activity.

6. A computerized health behavior reward system comprising:
   (a) a database storing data for:
      (1) a plurality of health programs and for each health program identifying:
         (A) identification data for said health program;
         (B) participation criteria for said health program; and
         wherein said health programs are selected from the group consisting of:
            (i) a preventive health program;
            (ii) a disease management program;
            (iii) an informational program regarding a health condition;
            (iv) a health assessment program;
            (v) a health coaching program;
            (vi) a health screening program;
            (vii) an exercise program;
            (viii) a wellness program: and
            (ix) a web-based health tool program;
      (2) a plurality of health activities for each of said programs selected from the group consisting of:
         (i) an enrollment activity; or
         (ii) a participation activity following an enrollment activity;
      (3) a reward associated with each of said health activities;
      (4) reward accounts for members of a rewards program;
   (b) a computer in communication with said database executing instructions to:
      (1) receive identifying data for a segmented group of members from a member population to target for participation in at least one of said health programs, said members identified for said segment based on an analysis of:
         (A) member health claim data; and
         (B) participation criteria for said least one of said health programs;
      (2) generate a list of members in said segment;
      (3) generate an offer to participate in said at least one of said health programs;
      (4) after said list and offer to participate are generated, transmitting to each member on said list said offer to participate;
      (5) receive responses from members in said segment to said offer to participate in said least one of said health programs; and
      (6) update at said computer said reward accounts for at least one of the following:
         (A) members in said segment completing an enrollment activity; and
         (B) members in said segment completing a participation activity that is part of a health activity after completing an enrollment activity;
      (j) wherein updating said reward accounts comprises issuing points that vary for each completed activity and are redeemable for merchandise, discounts or gift certificates.

7. The computerized system of claim 6 wherein said plurality of health programs are further selected from the group consisting of:
   (1) general health programs appropriate for all members; and
   (2) specialized health programs for members with specified health conditions.

8. The computerized system of claim 6 wherein said instruction to receive at said computer responses from said members in said segment comprises receiving responses through a reward account portal for said members.

9. The computerized system of claim 6 wherein said instruction to receive at said computer responses from said members in said segment comprises receiving at least one response through a computerized enrollment process completed for the member by a third party.

10. The computerized system of claim 6 wherein an offer to participate in said at least one of said health programs comprises an offer to complete an enrollment activity.

* * * * *